US008144956B2

(12) United States Patent
Salgo et al.

(10) Patent No.: US 8,144,956 B2
(45) Date of Patent: Mar. 27, 2012

(54) ULTRASONIC DIAGNOSIS BY QUANTIFICATION OF MYOCARDIAL PERFORMANCE

(75) Inventors: Ivan Salgo, Pelham, MA (US); Mary Kay Bianchi, Plaistow, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 792 days.

(21) Appl. No.: 12/282,657

(22) PCT Filed: Mar. 13, 2007

(86) PCT No.: PCT/IB2007/050842
§ 371 (c)(1),
(2), (4) Date: Sep. 12, 2008

(87) PCT Pub. No.: WO2007/107918
PCT Pub. Date: Sep. 27, 2007

(65) Prior Publication Data
US 2009/0136109 A1      May 28, 2009

Related U.S. Application Data

(60) Provisional application No. 60/784,194, filed on Mar. 20, 2006.

(51) Int. Cl.
*G06K 9/00*          (2006.01)
(52) U.S. Cl. .......................... 382/128; 382/103; 382/154
(58) Field of Classification Search ........................ None
See application file for complete search history.

(56) References Cited

U.S. PATENT DOCUMENTS

| 5,435,310 A | 7/1995 | Sheehan et al. | |
| 5,601,084 A * | 2/1997 | Sheehan et al. | 600/450 |
| 6,106,466 A * | 8/2000 | Sheehan et al. | 600/443 |
| 7,693,563 B2 * | 4/2010 | Suresh et al. | 600/407 |
| 2003/0236462 A1 | 12/2003 | Salgo et al. | |

FOREIGN PATENT DOCUMENTS

WO      2005/030057 A      4/2005

OTHER PUBLICATIONS

Stanley, T.E., et al., "Quantitative Analysis of Transesophageal Echocardiograms for the Intraoperative Setting: Clinical Need and Initial Experience," IEEE Engineering in Medicine and Biology Society 11th Annual International Conference, Nov. 9, 1989, pp. 1569-1670, XP010088564.

* cited by examiner

*Primary Examiner* — Minh N Tang
(74) *Attorney, Agent, or Firm* — W. Brinton Yorks, Jr.

(57) ABSTRACT

An ultrasonic diagnostic imaging system is described which acquires 3D data sets of the heart including the myocardium. The epicardial and endocardial surfaces of the myocardium in the data sets are identified by automated or semi-automated border detection. A 3D image of the myocardium is produced from the defined surfaces. The 3D image illustrates the wall thickness of the myocardium and can be segmented into defined regions, with quantified measures made for each defined region.

18 Claims, 9 Drawing Sheets

ULTRASONIC DIAGNOSIS BY QUANTIFICATION OF MYOCARDIAL PERFORMANCE

This invention relates to medical diagnostic ultrasound systems and, in particular, to ultrasound systems which perform quantified diagnostics of myocardial performance.

One of the parameters that is important for cardiac diagnosis is heart wall motion. In a healthy heart, the entire myocardial wall of the left ventricle (LV) moves strongly and in unison with each systolic contraction that pumps blood into the body's vascular system. A number of physiological factors can affect this myocardial motion. One is the supply of blood to the myocardium. When a patient suffers a heart attack, the flow of blood becomes obstructed in the coronary artery tree. A region of the myocardium that is denied a nourishing supply of blood will die and become damaged or infarcted. The infarcted region of the heart wall is no longer able to contract with the surrounding heart muscle as that portion of the muscle has become inert. The infarcted myocardium can be detected by careful observation of the heart wall motion. A scoring system has been developed by which segments or areas of the endocardium are quantitatively scored as to their motion. Such quantified measures can aid a cardiologist in determining the effect and extent of the infarction.

Another factor which affects myocardial motion is the synchronicity of the electrical signals that stimulate the heart motion. The electrical signals of the autonomous nervous system that stimulate myocardial contractions should be delivered to all regions of the myocardium in uniform order so that the entire myocardium will contract at the same time. This synchronicity can be assessed by observing the relative timing of movement of different areas of the heart wall. Quantified velocity measurements can be made of different areas of the wall of the LV during a complete cardiac cycle. Abnormalities of cardiac synchronization can be detected by comparing the times of occurrence of movement of different velocities. This diagnosis can lead to treatment by cardiac resynchronization therapy.

Yet another factor affecting heart wall motion is wall thickness. A clinician will often want to observe and measure the heart wall thickness at various locations and determine whether observed differences in thickness can be related to motional characteristics of the myocardium. Usually such observations are only made at suspect regions of the heart wall. It would be desirable, however, to have a complete record of heart wall thickness that can be related to an equally complete record of heart wall motion. It is further desirable for this record to be presented in a graphically intuitive way, and with quantified measures of wall thickening if desired.

In accordance with the principles of the present invention, a diagnostic ultrasound system and method are described which produces a three dimensional model of the myocardium. In an example shown below the three dimensional myocardial model is segmented with each segmented area depicting the heart wall thickness at that area. The thickness may be displayed either qualitatively, as by a color, or quantitatively. The motion of the wall segment may also be depicted if desired. The depicted information may also be shown in a two dimensional representation such as a polar or bulls-eye chart. In an example described below a three dimensional representation of the myocardium is produced automatically by automated border detection of a 3D data set of the heart.

Figure 3A:
Figure 3B:
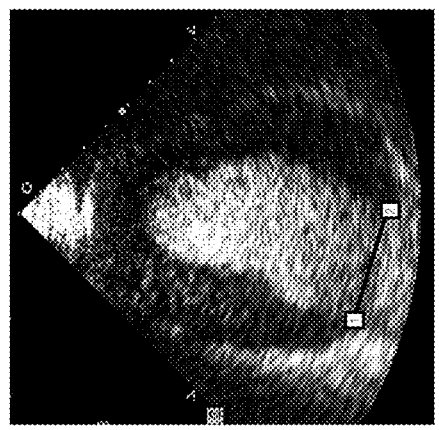
Figure 3C:
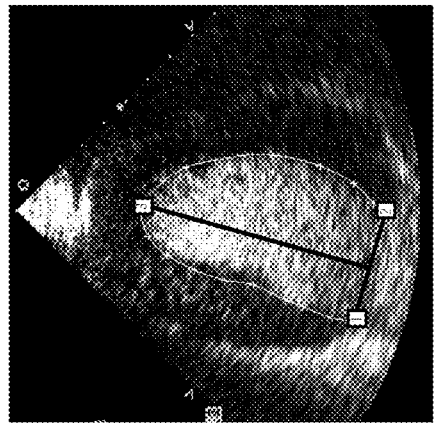

FIGS. 3a, 3b, and 3c illustrate the use of automated border detection to define the endocardial border of the left ventricle.

Figure 4:
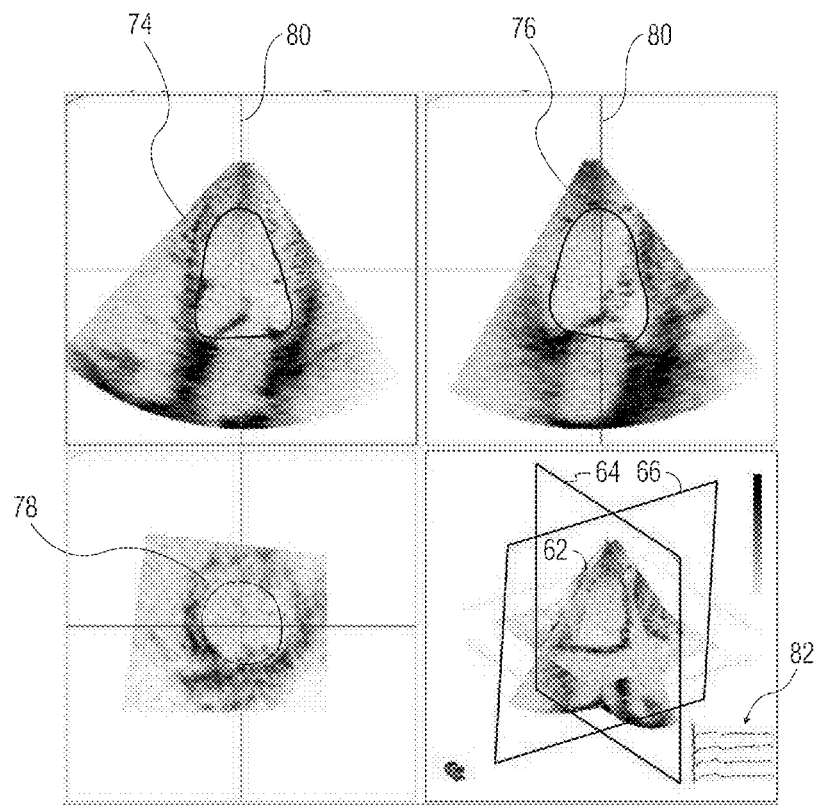

FIG. 4 illustrates the tracing of the endocardial border on the images of a 3D data set of the left ventricle at end diastole and the production of a model of the chamber volume of the left ventricle.

Figure 5:
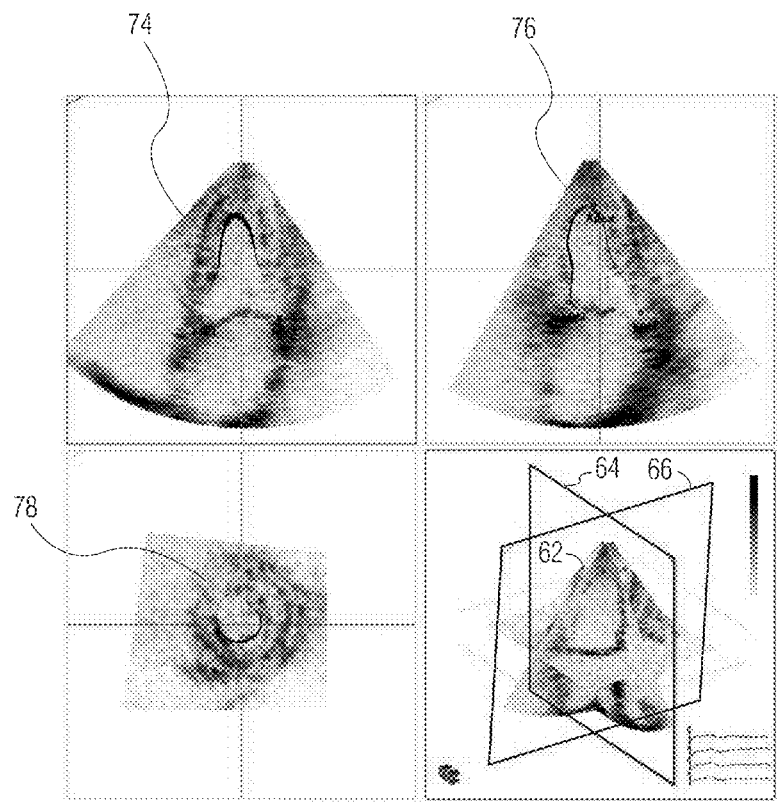

FIG. 5 illustrates the tracing of the endocardial border on the images of a 3D data set of the left ventricle at peak systole and the production of a model of the chamber volume of the left ventricle.

Figure 6:
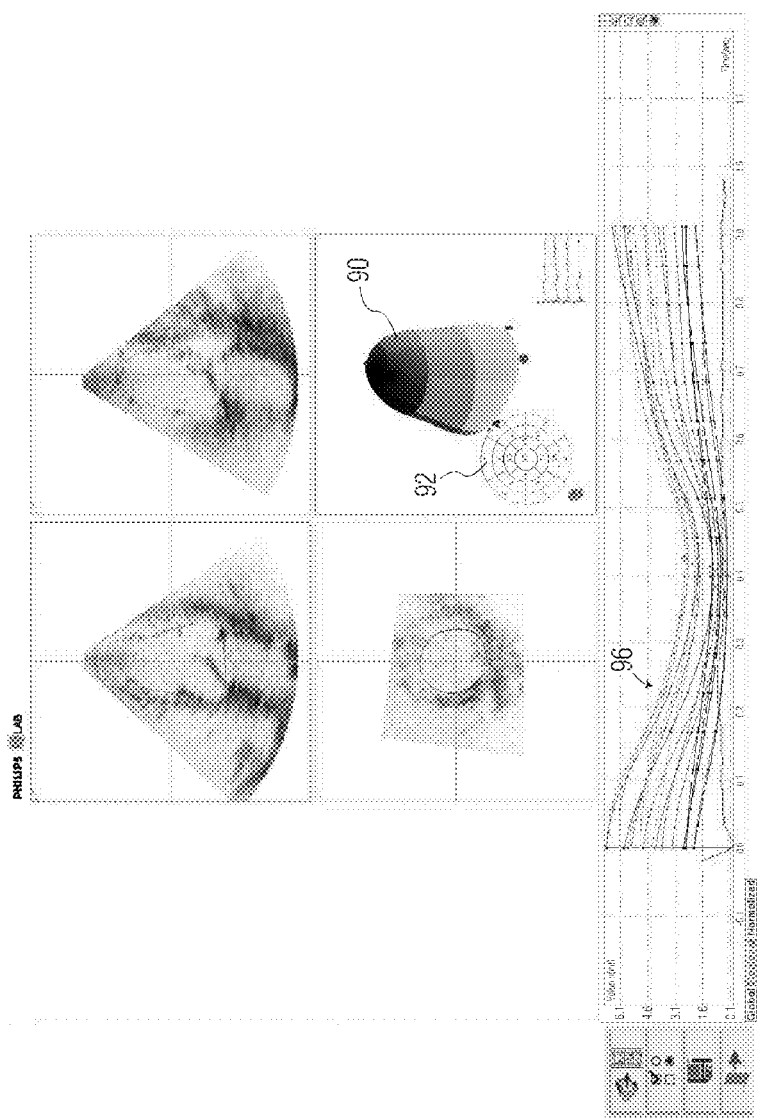

FIG. 6 illustrates a display of segmented ejection fraction volumes calculated from changes in the chamber volume over a heart cycle.

Figure 7:
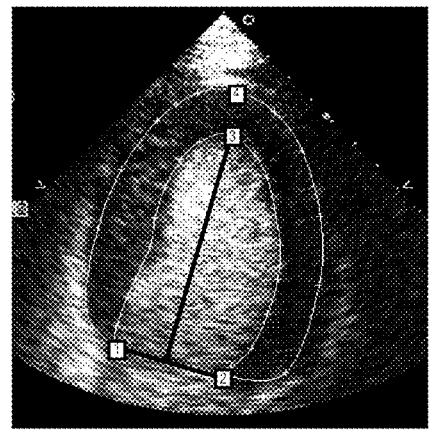

FIG. 7 illustrates the tracing of the epicardial and endocardial walls of the myocardium.

Figure 8:
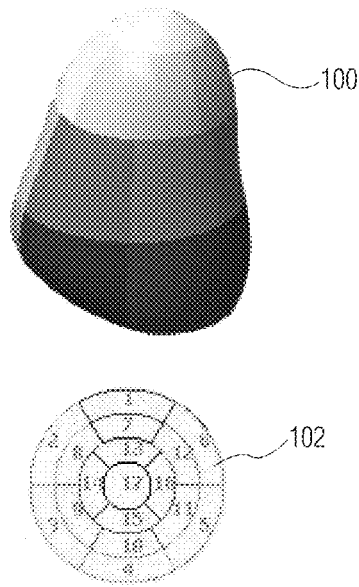

FIG. 8 illustrates a three dimensional representation of the myocardium produced in accordance with the principles of the present invention.

Figure 9:
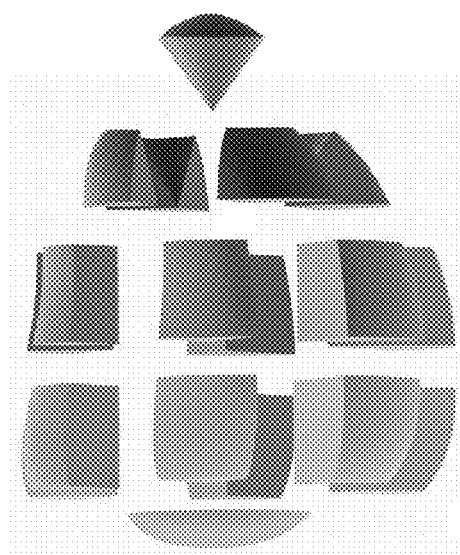

FIG. 9 is an exploded view of a segmented three dimensional representation of the myocardium produced in accordance with the principles of the present invention.

Figure 10:
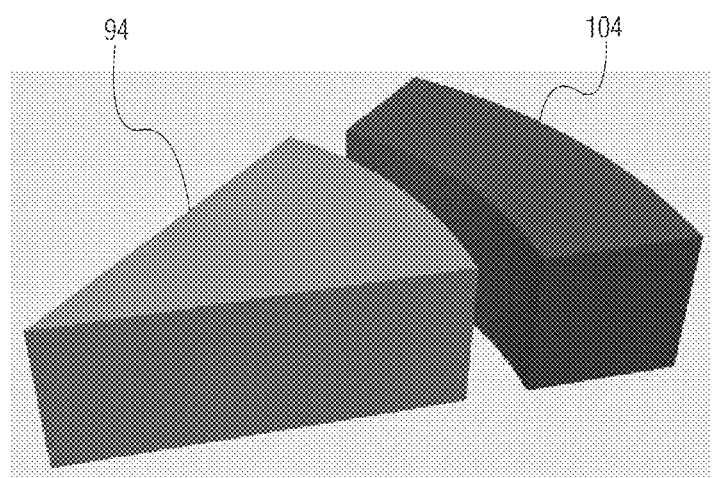

FIG. 10 illustrates a segment of a three dimensional representation of the myocardium and its corresponding segment of the heart chamber volume.

Figure 11:
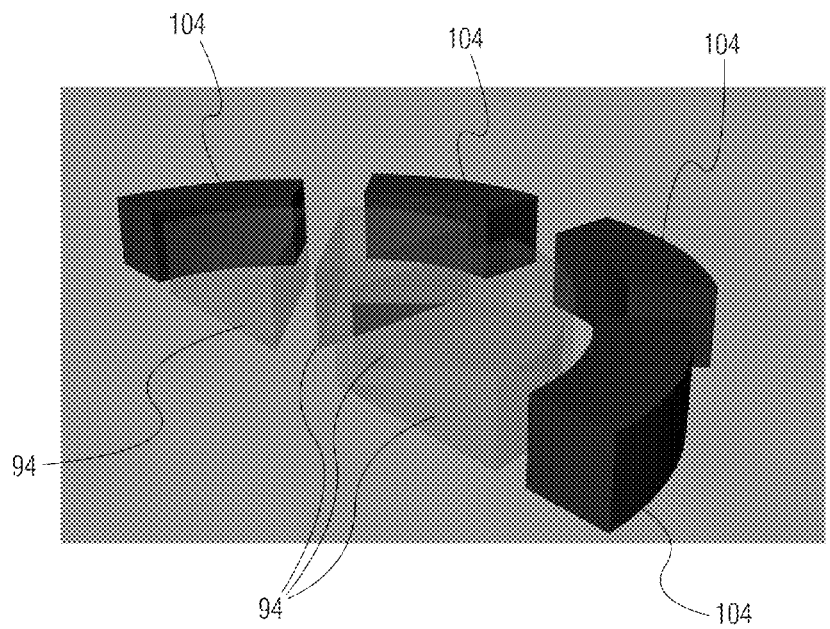

FIG. 11 illustrates an arc of segments of a three dimensional representation of the myocardium and their corresponding segments of the heart chamber volume.

Figure 12:
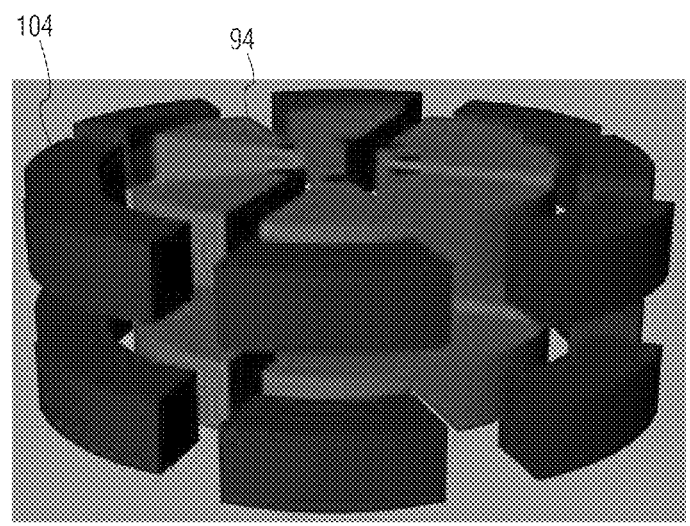

FIG. 12 is an exploded view of two full circumferences of segments of a three dimensional representation of the myocardium and their corresponding segments of the heart chamber volume.

Figure 1:
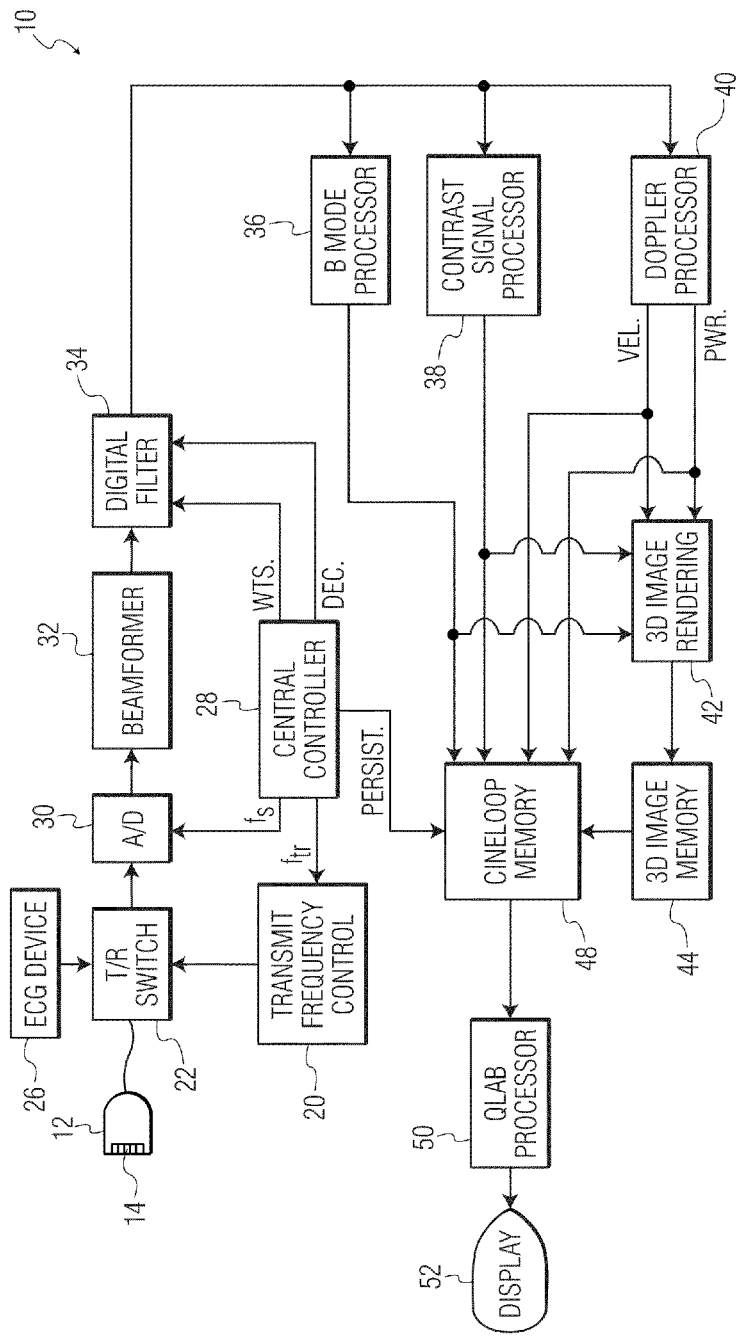
FIG. 1 illustrates in block diagram form an ultrasonic diagnostic imaging system constructed in accordance with the principles of the present invention.

Referring first to FIG. 1 an ultrasonic diagnostic imaging system constructed in accordance with the principles of the present invention is shown in block diagram form. An ultrasonic probe 12 includes an array 14 of ultrasonic transducers that transmit and receive ultrasonic pulses. The array may be a one dimensional linear or curved array for two dimensional imaging, or may be a two dimensional matrix of transducer elements for electronic beam steering in three dimensions. The three dimensional data sets and images described below are preferably acquired using a two dimensional array probe. The ultrasonic transducers in the array 14 transmit ultrasonic energy and receive echoes returned in response to this transmission. A transmit frequency control circuit 20 controls the transmission of ultrasonic energy at a desired frequency or band of frequencies through a transmit/receive ("T/R") switch 22 coupled to the ultrasonic transducers in the array 14. The times at which the transducer array is activated to transmit signals may be synchronized to an internal system clock (not shown), or may be synchronized to a bodily function such as the heart cycle, for which a heart cycle waveform is provided by an ECG device 26. When the heartbeat is at the desired phase of its cycle as determined by the waveform provided by ECG device 26, the probe is commanded to acquire an ultrasonic image. The frequency and bandwidth of the ultrasonic energy generated by the transmit frequency control circuit 20 is controlled by a control signal $f_{tr}$ generated by a central controller 28.

Echoes from the transmitted ultrasonic energy are received by the transducers in the array 14, which generate echo signals that are coupled through the T/R switch 22 and digitized by analog to digital ("A/D") converters 30 when the system uses a digital beamformer. Analog beamformers may also be used. The A/D converters 30 sample the received echo signals at a sampling frequency controlled by a signal $f_s$ generated by the central controller 28. The desired sampling rate dictated by sampling theory is at least twice the highest frequency of the received passband, and might be on the order of at least 30-40 MHz. Sampling rates higher than the minimum requirement are also desirable.

The echo signal samples from the individual transducers in the array 14 are delayed and summed by a beamformer 32 to form coherent echo signals. For 3D imaging with a two dimensional array, it is preferable to partition the beamformer between a microbeamformer located in the probe and the main beamformer in the system mainframe as described in U.S. Pat. No. 6,013,032 (Savord) and U.S. Pat. No. 6,375,617 (Fraser). The digital coherent echo signals are then filtered by a digital filter 34. In this embodiment, the transmit frequency and the receiver frequency are individually controlled so that the beamformer 32 is free to receive a band of frequencies which is different from that of the transmitted band such as a harmonic frequency band. The digital filter 34 bandpass filters the signals, and can also shift the frequency band to a lower or baseband frequency range. The digital filter could be a filter of the type disclosed in U.S. Pat. No. 5,833,613, for example. Filtered echo signals from tissue are coupled from the digital filter 34 to a B mode processor 36 for conventional B mode processing.

Filtered echo signals of a contrast agent, such as microbubbles, are coupled to a contrast signal processor 38. Contrast agents are often used to more clearly delineate the endocardial wall in relation to contrast agent in the blood pool of the heart chamber, or to perform perfusion studies of the microvasculature of the myocardium as described in U.S. Pat. No. 6,692,438 for example. The contrast signal processor 38 preferably separates echoes returned from harmonic contrast agents by the pulse inversion technique, in which echoes resulting from the transmission of multiple pulses to an image location are combined to cancel fundamental signal components and enhance harmonic components. A preferred pulse inversion technique is described in U.S. Pat. No. 6,186,950, for instance.

The filtered echo signals from the digital filter 34 are also coupled to a Doppler processor 40 for conventional Doppler processing to produce velocity and power Doppler signals. The output signals from these processors may be displayed as planar images, and are also coupled to a 3D image processor 42 for the rendering of three dimensional images, which are stored in a 3D image memory 44. Three dimensional rendering may be performed as described in U.S. Pat. No. 5,720, 291, and in U.S. Pat. Nos. 5,474,073 and 5,485,842, all of which are incorporated herein by reference.

The signals from the contrast signal processor 38, the B mode processor 36 and the Doppler processor 40, and the three dimensional image signals from the 3D image memory 44 are coupled to a Cineloop® memory 48, which stores image data for each of a large number of ultrasonic images. The image data are preferably stored in the Cineloop memory 48 in sets, with each set of image data corresponding to an image obtained at a respective time. The image data in a group can be used to display a parametric image showing tissue perfusion at a respective time during the heartbeat. The groups of image data stored in the Cineloop memory 48 may also be stored in a permanent memory device such as a disk drive or digital video recorder for later analysis. In this embodiment the images are also coupled to a QLAB processor 50, where the images are analyzed and three dimensional representations of the myocardium are produced as described below. The QLAB processor also makes quantified measurements of various aspects of the anatomy in the image and delineates tissue boundaries and borders by automated border tracing as described in US patent publication no. 2005-0075567 and PCT publication no. 2005/054898. The data and images produced by the QLAB processor are displayed on a display 52.

Figure 2:
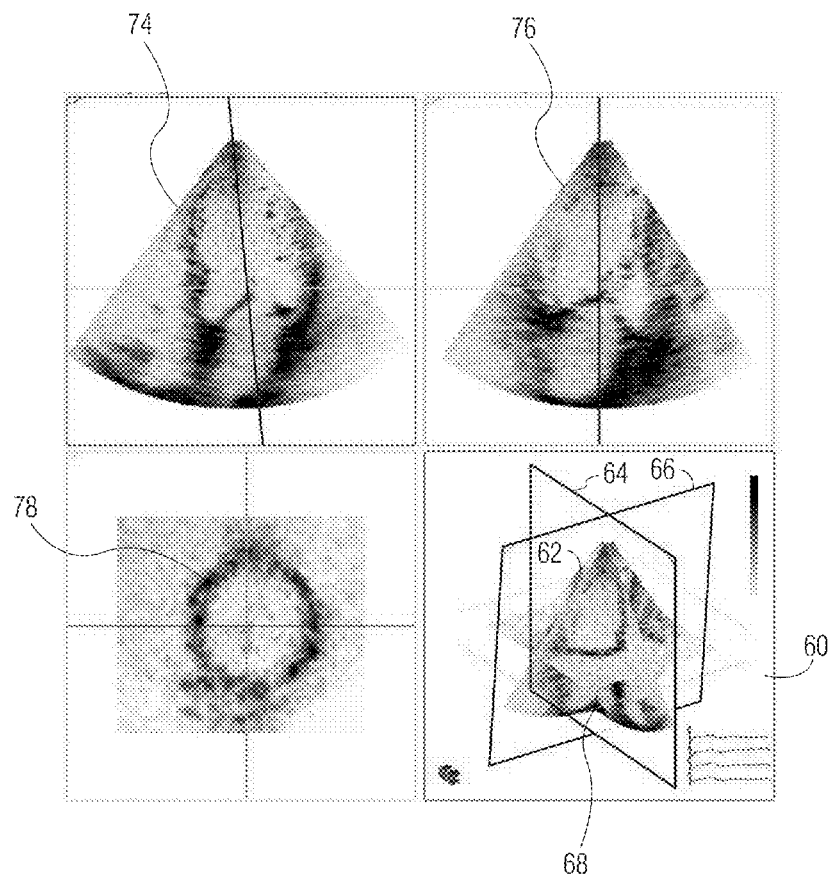
FIG. 2 illustrates a three dimensional image and two planar images produced from a 3D data set of the left ventricle.

The QLAB processor is capable of allowing a user to define two dimensional planes or slices of a three dimensional image. FIG. 2 illustrates a quad display produced by the QLAB processor 50 which displays a rendered 3D image in the lower right quadrant 60. The illustrated 3D image 62 is of the heart. The user is able to manipulate the controls of the ultrasound system to move and position three image planes over the 3D image 62, and the 2D images of those image planes are shown in the other quadrants of the display. In this example image plane 64 is positioned to produce the longitudinal image 74, the image plane 66 is positioned to produce the longitudinal image 76, and the transverse plane 68 is positioned to produce the transverse image 78. These images are produced from the values of the voxels of the 3D data set of the 3D image which are intersected (addressed) by the image plane locations. The lines drawn over the 2D images 74, 76, and 78 illustrate the intersection of the respective image planes with the other image planes of the 3D image 62.

The QLAB processor is capable of tracing the borders or boundaries of tissue structures in an image. This may be done by fully automated means as described in U.S. Pat. No. 6,491, 636, or by assisted automatic border detection as described in the aforementioned US patent publication no. 2005-0075567. The latter technique is conducted by first selecting an image which displays the boundary to be traced. FIGS. 3a, 3b, and 3c illustrate LV images in which the border of the LV is traced. The user designates a first landmark in the image with a pointing device such as a mouse or a trackball, usually located on the ultrasound system control panel or with the workstation keyboard, which manipulates a cursor over the image. In the example of FIG. 3a, the first landmark designated is the medial mitral annulus (MMA). When the user clicks on the MMA in the image, a graphic marker appears such as the white control point indicated by the number "1" in the drawing. The user then designates a second landmark, in this example the lateral mitral annulus (LMA), which is marked with the second white control point indicated by the number "2" in FIG. 3b. A line produced by the QLAB processor then automatically connects the two control points, which in the case of this longitudinal view of the left ventricle indicates the mitral valve plane. The user then moves the pointer to the endocardial apex, which is the uppermost point within the left ventricular cavity. As the user moves the pointer to this third landmark in the image, a template shape of the left ventricular endocardial cavity dynamically follows the cursor, distorting and stretching as the pointer seeks the apex of the chamber. This template, shown as a white line in FIG. 3c, is anchored by the first and second control points 1 and 2 and passes through the third control point, which is positioned at the apex when the user clicks the pointer at the apex, positioning the third control point 3. When positioned, the endocardial cavity template provides an approximate tracing of the endocardium as shown in FIG. 3c. In the embodiment of FIG. 3c a black line which bisects the left ventricle follows the pointer as it approaches and designates the apex. This black line is anchored between the center of the line indicating the mitral valve plane and the left ventricular apex, essentially indicating a center line between the center of the mitral valve and the apex of the cavity. In commercial implementations the QLAB™ processor is available onboard ultrasound systems or in offline workstation form from Philips Medical Systems of Andover, Mass. The automated border processing can be fully automated by other means.

Either of these or another border tracing technique are applied to the LV cavity as shown in the upper quadrants of the image of FIG. 4. The QLAB system applies the same technique to other planes (not shown) of the 3D image 62. These other planes may be chosen by moving the 2D image planes 64, 66 in angular increments around their line 80 of intersection and using the knowledge of the location of the adjacent border tracing to automatically draw the border in the current image, as described in the aforementioned U.S. Pat. No. 6,491,636. These borders of the longitudinal planes of the LV may be interconnected in a transverse plane to trace the endocardial border in the transverse image as shown in the lower left quadrant of FIG. 4.

In this example the initial tracing is done of the border when the heart is at end diastole. At end diastole the heart is fully expanded. This phase of the heart cycle can be found by scanning through successive images of the image sequence shown in FIGS. 2 and 4 with the trackball or other pointing device of the ultrasound system. Locating the end diastole image is assisted by the ECG trace 82 in the lower right corner of the 3D image quadrant. After the end diastole image has been located, the LV border is traced as previously described.

After the end-diastolic border is traced, the user scans through the images of the heart cycle to find the peak systolic image as shown in FIG. 5. The endocardial border is then drawn of the image set for peak systole as shown in FIG. 5. This is the point in the heart cycle at which the LV is most fully contracted. With these two limits of the heart volume defined, the QLAB processor traces the borders of the LV in the other 3D data sets of the heart cycle as described in the aforementioned U.S. Pat. No. 6,491,636. With the endocardial border now defined in three dimensions throughout a heart cycle, the volume of the LV can now be displayed in three dimensions as shown by the chamber volume 90 in the QLAB screen shot of FIG. 6. The outer surface of the volume 90 has been delineated by the previously described border tracing. The full heart cycle can be replayed, and the volume 90 dynamically changes throughout the heart cycle, continually contracting and expanding as the LV contracts and dilates with each contraction and expansion of the myocardium. The dynamic sequence can be stopped at any time and will appear as shown in FIG. 6. The dynamically moving planes and tracings shown in the other three quadrants will stop at the same time that the volume 90 is stopped, illustrating the traced endocardium in those planes at the same moment of the heart cycle. As the volume 90 is the volume of blood in the LV, the difference between the volume at end diastole and the volume at end systole is the ejection fraction. In this example the volume 90 is also segmented into different colored wedges. The outside of each wedge is shown by the different shading in FIG. 90. Each wedge is a pie-shaped volume segment between the outer surface of the volume 90 and the center line of the volume. The instantaneous and changing sizes of these volume segments can be shown in a chart such as the bulls-eye chart 92 shown next to the volume 90, in which each segment contains a numerical value of a volume segment at the moment that the dynamic display is stopped as shown in FIG. 6. The changing values of these volume segments are also displayed graphically by the QLAB system. The curves 96 at the bottom of the screen illustrate the changes of each of these volume segments over a complete heart cycle, which make up the full volume of the left ventricular heart chamber. Preferably each curve of the display 96 is color-coded to the color of the end surface of its corresponding wedge of volume 90, thus readily illustrating the correspondence.

In accordance with the principles of the present invention the QLAB processor 50 is also capable of tracing the epicardial border of the myocardium as shown in FIG. 7. The epicardial border tracing can be done in a continuous process starting with the endocardial identification steps illustrated in FIGS. 3a, 3b, and 3c. With the endocardial border thus defined, the user moves the cursor to the epicardial apex, the uppermost point on the outer surface of the myocardium. The user then clicks on the epicardial apex and a fourth control point marked "4" is positioned. A second trace then automatically appears which approximately delineates the epicardial border as shown in FIG. 7. This second trace, shown by the outer white border line in FIG. 7, is also anchored by the first and second control points and passes through the positioned fourth control point at the epicardial apex. The two traces are an approximate outline of the myocardial border.

As a final step, the user may want to adjust the traces shown in FIG. 7 so that they precisely outline the border of the myocardium. Located around each tracing are a number of small control points shown in the drawing as "+" symbols. The number and spacing of these small control points is a design choice or may be a variable that the user can set. The user can point at or near these control points and click and drag the outline to more precisely delineate the myocardial boundary. This process of stretching or dragging the border is known as "rubberbanding", and is described more fully in the aforementioned 6,491,636 patent, with particular reference to FIG. 9 of that patent. As an alternative to rubberband adjustment, in a more complex embodiment the approximated borders may automatically adjust to the image borders by image processing which uses the intensity information of the pixels at and around the approximated tissue borders. When finished, the border can precisely delineate the boundary of the myocardium by enclosing the image pixels of the myocardium in the image.

In accordance with the principles of the present invention the endocardial and epicardial borders are identified throughout the full 3D image data set and throughout the full heart cycle as illustrated previously for the endocardium in FIGS. 4 and 5. The identified endocardial borders define the inner surface of the myocardium and the identified epicardial borders define the outer surface of the myocardium. The coordinates of these two surfaces are applied to a 3D rendering algorithm to produce a myocardial thickness volume image 100 as illustrated in FIG. 8. The myocardial thickness volume 100 in FIG. 8 externally resembles the chamber volume 90 of FIG. 6 in this example. However, the myocardial thickness volume 100 is hollow, with the hollow space inside being the volume of the heart chamber inside the myocardium (chamber volume 90). The myocardial volume data set of a heart cycle can be replayed in real time, allowing the user to observe changes in the heart muscle over the full heart cycle. In this example the myocardial thickness volume 100 is segmented during the image processing, with each segment being delineated by a particular color or shading. The identified segments can then be individually scored or quantified by, for example, an algorithm calculating the average or mean distance between the defined inner and outer borders of each segment, which produces a measure of the myocardial wall thickness of each segment. These measures can be shown, for example, in a bulls-eye chart 102 with segments corresponding to the 3D segments of the myocardial volume. The numbers in each segment of the bulls-eye chart can indicate instantaneous or variations in the wall thickness of the corresponding 3D segments. Measurements can also be made and displayed indicating motion characteristics of the segments such as velocity, direction or distance traveled during a heartbeat, or strain or strain rate. Quantification can also be indicated for the perfusion characteristics of the segments. Since a rendering algorithm can be continuously executed with different viewing directions, the user can rotate the myocardial thickness volume 100 on the screen, stop and start its dynamic motion, view the volume semi-transparently as described in U.S. Pat. No. 5,720,291, view the volume in different cross-sectional views, or make measurements of the segments. A complete reference of the patient's myocardial performance can thus be saved and used for further diagnosis.

FIG. 9 is an exploded view of the myocardial thickness volume 100 of FIG. 8. This view illustrates that each segment of the thickness volume 100 represents a section of the myocardium, with a thickness depicting the actual instantaneous thickness of the myocardium at the time of acquisition of the 3D data set used to produce the volume image.

FIG. 10 illustrates how the segments of the chamber volume 90 fit inside the segments of the myocardial thickness volume 100. In this and the following examples the segments of the chamber volume and the segments of the myocardial volume are defined to be in corresponding alignment for ease of illustration. FIG. 10 shows a myocardial segment 104 in a partially exploded displacement from the corresponding segment 94 of the chamber volume (blood pool) inside the heart. The wedge-shaped chamber volume segment 94 terminated at the center line of the heart chamber at the pointed end of the wedge at the left in this example.

FIG. 11 illustrates this same alignment for a half circumference of myocardial segments 104 and chamber volume segments 94. In this illustration the chamber volume segments are displayed as partially transparent as described in PCT publication no. 2005/054898.

FIG. 12 is another example of a myocardial display of the present invention in which the segments 104 of two full circumferences of a myocardial volume are shown in a partially exploded view with segments 94 of a chamber volume located inside. In this example the segments of the two volumes are shown differently shaded. In a constructed embodiment the segments are shown with different color coding. Other uses and techniques for presenting a myocardial volume display of the present invention will readily occur to those skilled in the art. It will be recognized that various ultrasound techniques can be used to acquire a 3D data set for an implementation of the present invention, including B mode, contrast, and tissue Doppler acquisition modes. The technique described above is equally applicable to assessing the performance of other chambers of the heart such as the right ventricle. The technique of the present invention is also useful for tissue and organs other than the heart. For instance, the wall thickness of a blood vessel including possible obstructions in the blood vessel can be analyzed by use of the present inventive technique.

What is claimed is:

1. An ultrasonic diagnostic imaging system for illustrating tissue in three dimensions comprising:
    a 3D ultrasound data set of an object to be diagnosed;
    a border processor operable to identify opposing borders of the object in the data set; and
    a 3D image rendering processor responsive to the identification of the opposing borders of the object to produce a 3D image of the object including a thickness dimension of the object.

2. The ultrasonic diagnostic imaging system of claim 1, wherein the tissue comprises heart tissue and the object comprises the myocardium of a chamber of the heart.

3. The ultrasonic diagnostic imaging system of claim 2, wherein the chamber of the heart comprises one of the left ventricle or the right ventricle or the left atrium or the right atrium.

4. The ultrasonic diagnostic imaging system of claim 1, wherein the border processor comprises an automated or semi-automated border detection processor.

5. The ultrasonic diagnostic imaging system of claim 4, wherein the tissue comprises heart tissue and the automated or semi-automated border detection processor operates to identify the endocardial and epicardial borders of the myocardium.

6. The ultrasonic diagnostic imaging system of claim 5, wherein the 3D image rendering processor is responsive to the identification of the endocardial and epicardial borders to produce a 3D image of the myocardium including the myocardial thickness.

7. The ultrasonic diagnostic imaging system of claim 6, wherein the 3D image rendering processor further includes means for delineating segments of the myocardium.

8. The ultrasonic diagnostic imaging system of claim 7, further comprising a quantification algorithm responsive to the delineation of segments of the myocardium which acts to produce a quantified measurement of a segment of the myocardium.

9. The ultrasonic diagnostic imaging system of claim 8, wherein the quantified measurement is of the thickness of a segment of the myocardium.

10. The ultrasonic diagnostic imaging system of claim 8, wherein the quantified measurement is of at least one of the velocity, direction, distance traveled, strain, strain rate, thickening or perfusion characteristic of a segment of the myocardium.

11. The ultrasonic diagnostic imaging system of claim 1, wherein the 3D image of the object further includes the delineation of segments of the object;
    and further comprising a display of quantified measures corresponding to the segments.

12. The ultrasonic diagnostic imaging system of claim 1, further comprising means for displaying the 3D image of the object semi-transparently.

13. The ultrasonic diagnostic imaging system of claim 1, further comprising means for displaying the 3D image of the object in cross section.

14. The ultrasonic diagnostic imaging system of claim 1, wherein the 3D image of the object further includes the delineation of segments of the object;
    further comprising means for displaying the 3D image of the object in an exploded view of the segments.

15. The ultrasonic diagnostic imaging system of claim 1, wherein the tissue comprises heart tissue;
    and further comprising producing a succession of 3D images of the heart over a heart cycle for a real time display.

16. A method for ultrasonically displaying at least a portion of an organ having an inner surface and an outer surface comprising:
    acquiring a 3D data set of at least a portion of an organ including at least a portion of the inner surface and the outer surface of the organ;
    identifying the inner surface and the outer surface by border detection;
    rendering a 3D image of the at least a portion of the organ in response to the border detection of the inner surface and the outer surface including a thickness dimension between the inner and outer surfaces.

17. The method of claim 16, wherein the organ comprises the heart and the portion comprises the myocardium,
wherein acquiring further comprises acquiring a plurality of 3D data sets over a heart cycle;
wherein identifying further comprises identifying the endocardial and epicardial surfaces of the myocardium; and
wherein rendering further comprises rendering a 3D image of the myocardium including the myocardial thickness.

18. The method of claim 17, further comprising:
identifying segments of the 3D image of the myocardium; and
producing quantified measures of the identified segments.

* * * * *